(12) United States Patent
An et al.

(10) Patent No.: US 10,945,670 B2
(45) Date of Patent: Mar. 16, 2021

(54) MINUTE VOLUME SENSOR OPTIMIZATION USING QUADRIPOLAR LEADS

(71) Applicant: Cardiac Pacemakers, Inc., St. Paul, MN (US)

(72) Inventors: Qi An, Blaine, MN (US); Yinghong Yu, Shoreview, MN (US); Yi Zhang, Plymouth, MN (US); Viktoria A. Averina, Shoreview, MN (US); Pramodsingh Hirasingh Thakur, Woodbury, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 69 days.

(21) Appl. No.: 15/642,512

(22) Filed: Jul. 6, 2017

(65) Prior Publication Data

US 2018/0008197 A1  Jan. 11, 2018

Related U.S. Application Data

(60) Provisional application No. 62/358,981, filed on Jul. 6, 2016.

(51) Int. Cl.
*A61B 5/00* (2006.01)
*A61N 1/365* (2006.01)
(Continued)

(52) U.S. Cl.
CPC .............. *A61B 5/686* (2013.01); *A61B 5/076* (2013.01); *A61B 5/0809* (2013.01); *A61B 5/4836* (2013.01); *A61B 5/7203* (2013.01); *A61B 5/7278* (2013.01); *A61B 5/7285* (2013.01); *A61N 1/368* (2013.01); *A61N 1/36521* (2013.01); *A61N 1/36535* (2013.01);
(Continued)

(58) Field of Classification Search
None
See application file for complete search history.

(56) References Cited

U.S. PATENT DOCUMENTS

| 6,076,015 | A | 6/2000 | Hartley et al. |
| 9,037,239 | B2 * | 5/2015 | Brooke .............. A61N 1/36185 607/27 |

(Continued)

*Primary Examiner* — Michael W Kahelin
*Assistant Examiner* — Elizabeth K So
(74) *Attorney, Agent, or Firm* — Schwegman Lundberg & Woessner, P.A.

(57) ABSTRACT

An apparatus comprises a respiration sensing circuit configured for coupling electrically to a plurality of electrodes and for sensing a respiration signal representative of respiration of a subject; a signal processing circuit electrically coupled to the respiration sensing circuit and configured to extract a respiration parameter from a sensed respiration signal and determine a signal performance metric for the sensed respiration signal using the respiration parameter; and a control circuit. The control circuit is configured to: initiate sensing of a plurality of respiration signals using different electrode combinations of the plurality of electrodes and determining of the signal performance metric for the sensed respiration signals; and enable an electrode combination from the plurality of electrodes and for use in monitoring respiration of the subject according to the signal performance metric.

20 Claims, 4 Drawing Sheets

(51) Int. Cl.

| | | |
|---|---|---|
| *A61B 5/08* | (2006.01) | |
| *A61N 1/368* | (2006.01) | |
| *A61B 5/0205* | (2006.01) | |
| *A61B 5/053* | (2006.01) | |
| *A61B 5/091* | (2006.01) | |
| *A61B 5/07* | (2006.01) | |
| *A61B 5/042* | (2006.01) | |
| *A61B 5/0538* | (2021.01) | |
| *A61B 5/11* | (2006.01) | |

(52) U.S. Cl.
CPC ........... *A61B 5/0205* (2013.01); *A61B 5/0422* (2013.01); *A61B 5/0538* (2013.01); *A61B 5/0816* (2013.01); *A61B 5/091* (2013.01); *A61B 5/1116* (2013.01); *A61B 5/7221* (2013.01); *A61B 2562/0209* (2013.01)

(56) References Cited

U.S. PATENT DOCUMENTS

2005/0182447 A1* 8/2005 Schecter .............. A61N 1/3627
607/2
2016/0331273 A1* 11/2016 Armoundas ............. A61B 5/72

\* cited by examiner

MINUTE VOLUME SENSOR OPTIMIZATION USING QUADRIPOLAR LEADS

CLAIM OF PRIORITY

This application claims the benefit of priority under 35 U.S.C. § 119(e) of U.S. Provisional Patent Application Ser. No. 62/358,981, filed on Jul. 6, 2016, which is herein incorporated by reference in its entirety.

BACKGROUND

Ambulatory medical devices include implantable medical devices (IMDs), wearable medical devices, handheld medical devices, and other medical devices. Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition.

Some implantable medical devices can be diagnostic-only devices, such as implantable loop recorders (ILRs) and subcutaneously implantable heart failure monitors (SubQ HFMs). The devices may include electrodes in communication with one or more sense amplifiers to monitor electrical heart activity within a patient, or can include one or more sensors to monitor one or more other internal patient parameters. Subcutaneously implantable devices may include electrodes that are able to sense cardiac signals without being in direct contact with the patient's heart. Other examples of IMDs include implantable drug delivery systems or implantable devices with neural stimulation capability (e.g., vagus nerve stimulator, baroreflex stimulator, carotid sinus stimulator, spinal cord stimulator, deep brain stimulator, etc.).

Some medical devices include one or more sensors to monitor different physiologic aspects of the patient. For example, the devices may derive measurements associated with a cardiac depolarization or with respiration of the patient. The measurements can provide useful information concerning the health of the patient. Knowledge regarding the onset of a physiological condition can be useful to physicians and clinicians for diagnostic purposes or to tailor performance of a medical device to that patient's needs to provide the most effective patient therapy.

Overview

It can be desirable for ambulatory medical devices to collect accurate information used to monitor the physiological health of the patient, such as respiration data for example. Accurate patient information can help to provide the most effective device-based therapy or non-device based therapy for the patient. The present subject matter relates to improving monitoring of patient respiration.

One example apparatus of the present subject matter can include a respiration sensing circuit configured for coupling electrically to a plurality of electrodes and for sensing a respiration signal representative of respiration of a subject; a signal processing circuit electrically coupled to the respiration sensing circuit and configured to extract a respiration parameter from a sensed respiration signal and determine a signal performance metric for the sensed respiration signal using the respiration parameter; and a control circuit. The control circuit is configured to: initiate sensing of a plurality of respiration signals using different electrode combinations of the plurality of electrodes and determining of the signal performance metric for the sensed respiration signals; and enable an electrode combination from the plurality of electrodes and for use in monitoring respiration of the subject according to the signal performance metric.

This section is intended to provide a brief overview of subject matter of the present patent application. It is not intended to provide an exclusive or exhaustive explanation of the invention. The detailed description is included to provide further information about the present patent application such as a discussion of the dependent clams and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other ambulatory device need not include all of the features described herein, but may be implemented to include selected features that provide for unique structures or functionality. Such a device may be implemented to provide a variety of therapeutic or diagnostic functions.

As explained previously, respiration information can provide valuable information related to a patient's health. This information can be used to adjust not only device-based therapy or non-device based treatment for the patient, but also to identify those patients who are at risk and to help allocate medical care resources accordingly. Device-based monitoring can collect respiration information throughout the day and for varying patient activity. Thus, device-based monitoring can provide advantages over monitoring that is limited to a clinical setting.

Figure 1:
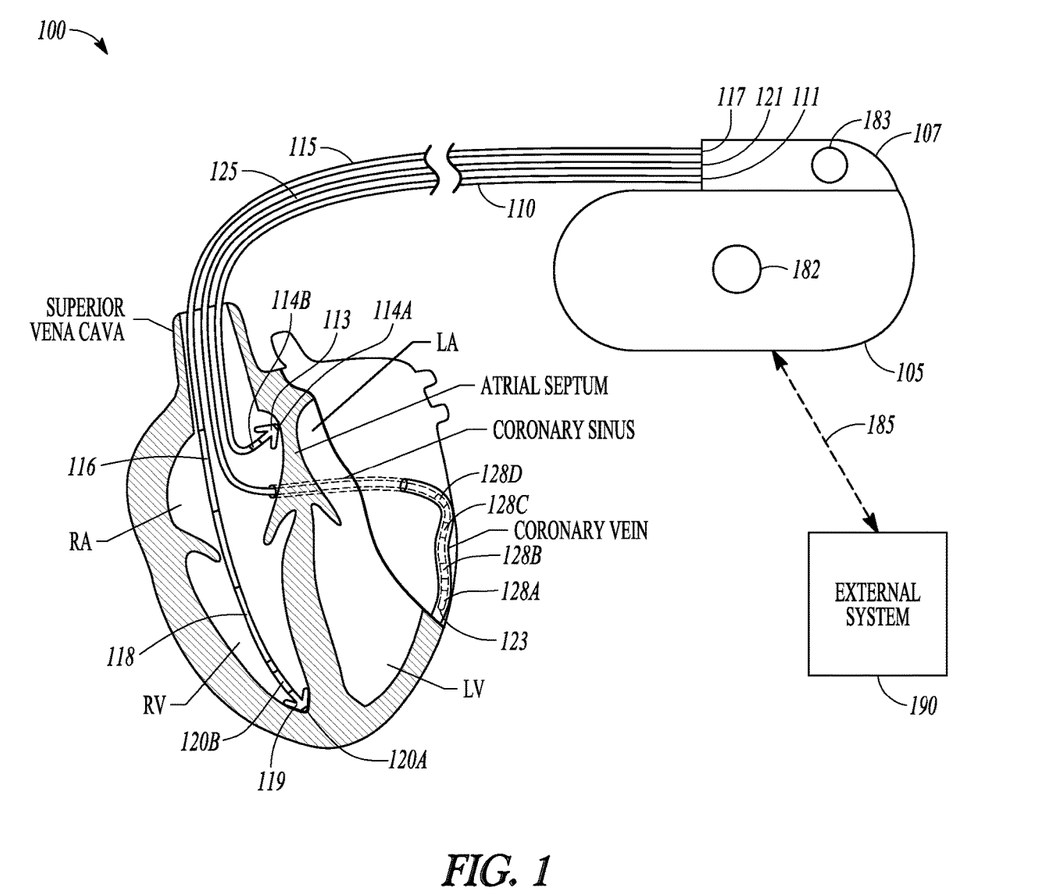
FIG. 1 is an illustration of an example of portions of a medical device system that includes an ambulatory medical device.

FIG. 1 is an illustration of portions of a system 100 that uses an IMD 105. Examples of the IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes a right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV electrodes 120A and 120B, or an electrode formed on the can of IMD 105, allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV tip electrode 128A and LV ring electrodes 128B, 128C, and 128D. The distal portion of the LV lead 125 is configured for placement in the coronary sinus and coronary vein such that the LV electrodes 128A, 128B, 128C, and 128D are placed in the coronary vein. Any combination of the LV electrodes 128A, 128B, 128C, and 128D may form a bipolar electrode pair and are typically incorporated into the lead body at distal end 123. Each can be electrically coupled to IMD 105 such as through one or more conductors extending within the lead body. LV tip electrode 128A, LV ring electrodes 128B, 128C, and 128D, or an electrode 182 formed on the can of the IMD 105 allow for sensing an LV electrogram signal representative of LV depolarizations and delivering LV pacing pulses.

As explained previously herein, the ambulatory medical device such as the IMD shown in the example of FIG. 1 can provide electrogram sensing. The device may be configured to sense other types of physiological signals, such as sense signals representative of physiological impedance. For instance, an electrical current could be applied between an RV electrode (e.g., RV electrode 120B) and an electrode 182 formed on the device can using a stimulus circuit. Voltage resulting from the applied current can be measured using another RV electrode (e.g., electrode 118) and an electrode 183 formed on the device header. Combinations involving LV electrodes can be used similarly. Impedance across at least a portion of the thorax region of the subject may then be calculated using Ohms Law.

The signal representative of physiological impedance can vary with respiration of the subject to provide respiration information. The impedance sensor can therefore be used as a respiration sensor to measure respiration parameters such as respiratory rate, tidal volume, minute respiration volume, and derived parameters (e.g., the ratio of respiratory rate over tidal volume). An approach to monitoring thoracic impedance is described in Hartley et al., U.S. Pat. No. 6,076,015, "Rate Adaptive Cardiac Rhythm Management Device Using Transthoracic Impedance," filed Feb. 27, 1998, which is incorporated herein by reference in its entirety.

An arrangement of electrodes such as those shown in the example of FIG. 1 can be used to measure impedance in multiple directions. This is sometimes called measuring impedance vectors. For example, impedance measured between LV ring electrode 128B and an electrode formed on the can or the header of the IMD can be a first impedance vector, and impedance measured between the LV ring electrode 128D and an electrode formed on the can or the header of the IMD can be a second impedance vector.

The example of FIG. 1 also shows that because there may be multiple electrodes disposed in or more of the RA, RV, and LV, there may be many options available for impedance vectors to use in sensing respiration information. It may be desirable for the medical device to automatically identify the best or optimum combination of electrodes to use in monitoring respiration of the patient or subject.

Figure 2:
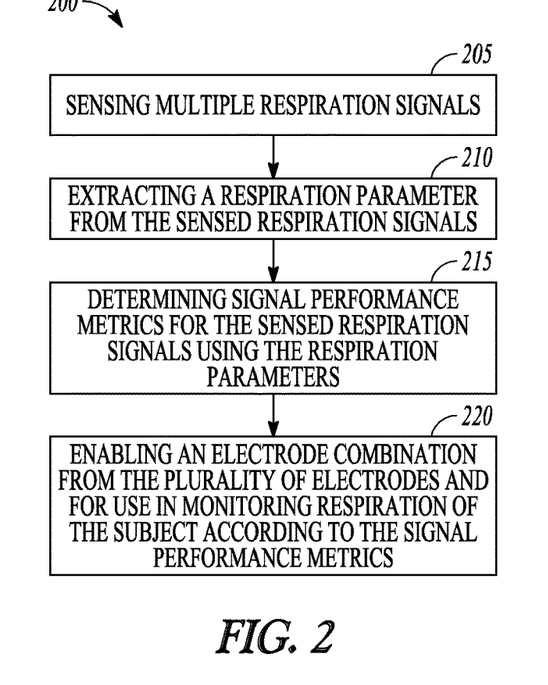
FIG. 2 is a flow diagram of a method of controlling operation of an ambulatory medical device.

FIG. 2 is a flow diagram of a method of controlling operation of an ambulatory medical device. At 205, multiple respiration signals are sensed using a sensing circuit and using different combinations of electrodes of the medical device. A respiration signal includes respiration information of a subject.

At 210, a respiration parameter is extracted from the sensed respiration signals. An example of a respiration parameter is respiration tidal volume (TV). In some examples, the respiration is an impedance signal that is calibrated for respiration of the subject. TV can be extracted from the impedance signal.

At 215, a signal performance metric is determined for the sensed respiration signals using the extracted respiration parameter. In an example, if the extracted respiration parameter is TV, the signal performance metric can be a signal to nose ratio (SNR) determined using the TV parameters. For instance, SNR for TV may be calculated as ratio of the mean of the TV parameter values to the standard deviation of the TV parameter values or $SNR=(TV_{MEAN}/TV_{STD})$.

At 220, an electrode combination is enabled, from the multiple electrode combinations available for use in monitoring respiration, according to the signal performance metric. For example, a large SNR may indicate that the TV measured from a particular electrode combination is less noisy.

In some embodiments, the selected electrode combination is used to monitor minute ventilation (MV) of the subject. MV may be determined according to $MV=TV \times RR$, where RR is respiration rate. RR may be determined from the same sensor circuit, or from a different sensor circuit. For instance, TV and RR may both be determined from the same impedance signal, or TV may be determined from the impedance signal and RR may be determined using a sensed accelerometer signal representative of motion of the subject's respiration.

Figure 3:
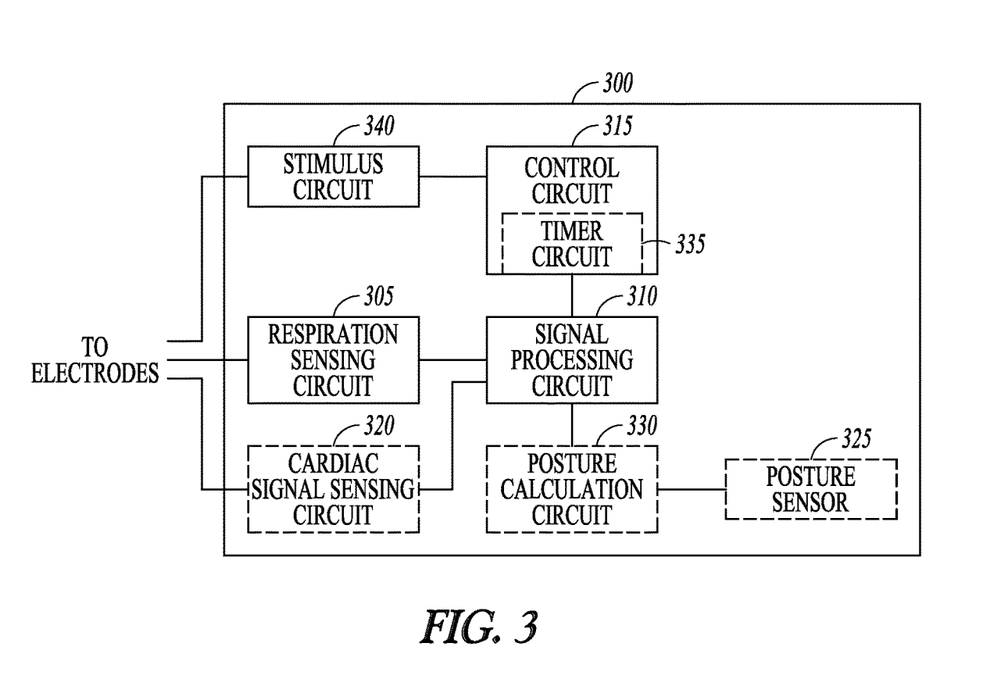
FIG. 3 is a block diagram of portions of an example of an ambulatory medical device.

FIG. 3 is a block diagram of portions of an example of an ambulatory medical device. The device 300 includes a respiration sensing circuit 305, a signal processing circuit 310, and a control circuit 315. The control circuit 315 can include a processor such as a microprocessor, a digital signal processor, application specific integrated circuit (ASIC), or other type of processor, interpreting or executing instructions in software modules or firmware modules. The control circuit 315 may include other circuits or sub-circuits to perform the functions described. These circuits may include software, hardware, firmware or any combination thereof. Multiple functions can be performed in one or more of the circuits or sub-circuits as desired. The signal processing circuit 310 may be included in the control circuit 315 or may be a circuit separate from the control circuit (e.g., a separate processor).

The device 300 may include a switching circuit (not shown) to electrically couple different combinations of electrodes to the respiration sensing circuit 305. Combinations of the electrodes may be arranged to include a significant portions of the subject's thorax region between the electrodes. For instance, the electrode combinations may include at least one electrode implantable in the RA, RV, or LV of the subject and an electrode formed on housing or the header of the device. The respiration sensing circuit 305 generates a sensed signal that is representative of respiration. In some embodiments, the respiration sensing circuit 305 includes an impedance sensing circuit, and impedance signals sensed by the impedance sensing circuit are representative of respiration of the subject.

The control circuit 315 determines the best or optimum combination of electrodes to use in monitoring respiration of the subject. To determine the best electrode combination, the control circuit 315 initiates sensing of multiple respiration signals. The signal processing circuit 310 extracts a respiration parameter from a sensed respiration signal and determines a signal performance metric for the sensed respiration signal using the respiration parameter. Using the signal performance metrics, the control circuit 315 enables an electrode combination from the plurality of electrodes for use in monitoring respiration of the subject. In some embodiments, the respiration parameter is TV, and the signal performance metric includes a SNR calculated using measured tidal volume.

In some embodiments, the respiration parameter extracted from the respiration signal is RR. If the respiration signal is a noisy signal, the signal processing circuit 310 may not be able to extract RR information from the signal. If a specific electrode combination is less noisy than other combinations, more RR information may be available for that electrode combination. In some embodiments, the signal performance metric for an electrode combination is the amount of RR information available. For instance, the control circuit 315 initiates RR measurements for the electrode combinations and tracks the amount of time that obtaining RR information was successful. The signal performance metric for an electrode combination may be the percentage of time or the percentage of attempts that RR information was available and collected for the electrode combination. This approach may be useful for right-sided implants wherein the device is implanted in a subcutaneous pocket on the right side of the patient. Right-side implants may be more susceptible to interference in sensing the signals, which may result in more RR measurement being unsuccessful.

The control circuit 315 may use additional criteria to select the electrode combination to use in monitoring respiration. In some embodiments, the device 300 includes a cardiac signal sensing circuit 320 that can be selectively coupled to the electrodes to sense electrical cardiac activation within the subject's body. In some examples, sensed cardiac signals are used to detect tachyarrhythmia such as ventricular tachycardia. The control circuit 315 may select the electrode combination to use in monitoring respiration that would have a low adverse impact on the sensing of tachyarrhythmia. As explained previously herein, respiration sensing may include applying current to electrodes and sensing the resulting voltage. The applied current may lead to over-sensing by the cardiac signal sensing circuit 320. The control circuit 315 may select electrodes that are less likely to interfere with cardiac signal sensing, such as selecting electrodes according to the physical separation of the respiration sensing electrodes and the tachyarrhythmia detecting electrodes.

The respiration information may be used to adjust device settings. In some examples, the sensed electrical cardiac activation signals are used to control delivery of pacing therapy to treat bradycardia. The device 300 may include a stimulus circuit 340 that provides pacing stimulation therapy to the subject. The control circuit may use the respiration information to adjust a cardiac pacing therapy parameter. For instance, the control circuit may use MV information to detect that there is more demand for cardiac output for the subject (e.g., the subject is exercising). The control circuit 315 may increases the heart rate of the subject using the pacing therapy in response to the detected change in MV.

The optimal combination of electrodes to use in monitoring respiration may change with posture of the subject. In some examples, the device 300 includes a posture sensor 325 that provides posture signal that includes posture information of the subject. Examples of a posture sensor include a multi-axis accelerometer and a tilt switch. With a posture sensor, the device 300 can detect whether a patient is in an upright position, a supine position, a prone position, on his or her left or right side, or if the patient is in a tilted position.

The device may include a posture calculation circuit 330 that determines posture of the subject using the posture information. The control circuit 315 initiates sensing of respiration signals using different electrode combinations of electrodes for different postures, and initiates determining the signal performance metric for the different postures. The control circuit 315 enables the electrode combination for respiration monitoring using the signal performance metric and the determined posture of the subject.

Respiration information for a subject may be more useful at certain times of the day than other times. For instance, the device 300 may be used to collect respiration data for apnea detection and respiration data collected at night when the patient is sleeping may be more useful. In some examples, the device includes a timer circuit 335 that may be integral to, or electrically coupled to, the control circuit 315. The control circuit 315 initiates the sensing of the respiration signals using different electrode combinations and determines the signal performance metric for the sensed respiration signals according to a time of day. The control circuit 315 may select the electrode combination for use in monitoring MV of the subject according to the signal performance metric and the time of day. In some examples, the timer circuit 335 can be used to trigger optimization of the electrodes used for respiration monitoring according to a schedule.

As explained previously in regard to FIG. 1, some implantable electrodes usable for sensing respiration can be included in a LV lead 125 configured for placement or insertion in the coronary vein. The best electrode combination for respiration monitoring may include an electrode of LV lead 125 not contacting the coronary vein and an electrode formed on the housing or header of the device.

Figure 4:
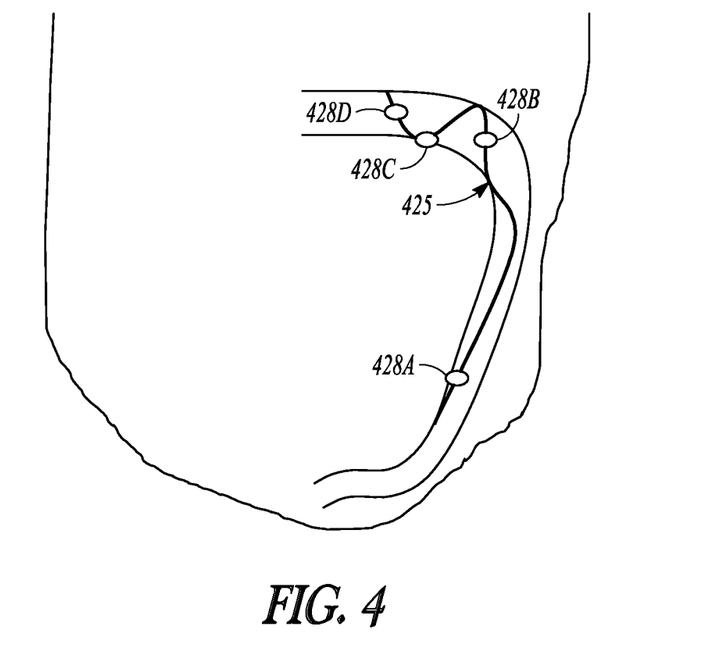
FIG. 4 is an illustration of an example of a cardiac lead implanted in a coronary vein of the left ventricle.

FIG. 4 is an illustration of an example of portions of a cardiac lead implanted in a coronary vein of the LV. The LV lead 425 includes four LV electrodes 428A, 428B, 428C, and 428D. In the example, LV electrodes 428A and 428C contact the wall of the coronary vein and electrodes 428B and 428D do not contact the wall of the coronary vein. A non-contacting electrode is merged in the blood pool and has minimal impact from the contact impedance of the coronary vein tissue. Thus, a non-contacting electrode will have lower impedance than a contacting electrode and will likely have a better SNR for sensed signals. Therefore, it is more desirable to select a non-contacting electrode for respiration sensing than a contacting electrode. Additionally, electrodes contacting the wall of the coronary vein are better suited for sensing intrinsic cardiac signal and delivering pacing therapy. Using non-contacting electrodes for respiration sensing will not interfere with pacing therapy. Knowledge of which electrodes contact the coronary vein and which electrodes do not contact the coronary vein allows the device 300 to select non-contacting electrodes for respiration sensing and select contacting electrodes to deliver pacing therapy to the LV.

Figure 5:
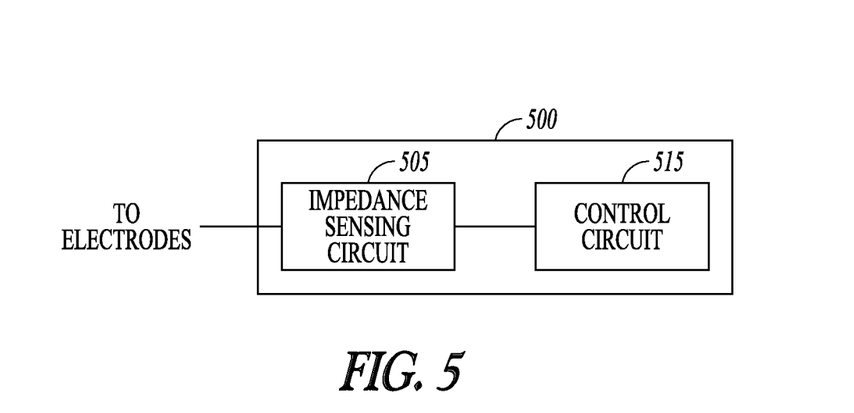
FIG. 5 is a block diagram of portions of an example of an ambulatory medical device.

FIG. 5 is a block diagram of portions of an example of an ambulatory medical device. The device 500 includes an impedance sensing circuit 505 for sensing an impedance signal representative of respiration and a control circuit 515. The control circuit 515 is electrically coupled to the impedance sensing circuit and initiates sensing values of impedance of different electrode combinations. The impedance sensing circuit 505 can be electrically coupled to electrodes that are implantable in the coronary vein and to electrodes formed on a housing of the device 500 or a header of the device 500. To identify an electrode that is not in contact with the wall of the coronary vein, the control circuit 515 initiates sensing values of impedance of different electrode combinations that include the electrodes in the coronary vein and an electrode on the device housing or header. The electrode combination with the lowest impedance is selected for use with the impedance sensing circuit in monitoring respiration of the subject. The device may also assess SNR calculated using a respiration parameter in addition to the impedance determination. The device may include additional circuits to provide therapy to the subject (e.g., pacing therapy). As explained previously the device 500 may adjust therapy settings based on the respiration information.

Another approach to determining whether an electrode is a non-contacting electrode is to determine stimulation energy thresholds for cardiac capture. Cardiac capture refers to an evoked response that occurs as a result of the pacing stimulation. Contacting electrodes will have a lower threshold for cardiac capture than non-contacting electrodes. Selecting electrode combinations with the highest capture thresholds as candidates for respiration monitoring may reduce interference with pacing that uses an electrode combination with the lowest capture threshold.

Returning to the example of FIG. 3, the device 300 may include the respiration sensing circuit 305, the cardiac signal sensing circuit 320, the stimulus circuit 340, and the control circuit 315. Capture threshold tests are performed to determine capture threshold levels for electrode combinations that include LV electrodes located in the coronary vein. The control circuit 315 initiates delivery of pacing pulses using combinations of the electrodes that include one electrode in the LV as a pacing cathode and the other electrodes as the pacing anode (e.g., one of the other LV electrodes, an RV electrode, or a can electrode as the anode).

The control circuit 315 initiates sensing of cardiac activation resulting from the pacing pulses and determines a cardiac capture pulse energy level threshold for the electrodes using the sensed cardiac activation. The device may include the signal processing circuit 310 to determine the cardiac capture pulse energy level thresholds. The control circuit 315 enables an electrode combination from the plurality of electrodes having the highest determined cardiac capture pulse energy level threshold for use in monitoring respiration. In certain examples, the electrode combination is used to monitor MV of the subject. In certain examples, an electrode combination with the lowest determined cardiac capture pulse energy level threshold is enabled for delivering pacing therapy.

The devices, methods and systems described herein provide device-recorded information related to respiration of the patient or subject. The configuration of the electrodes used to sense the respiration signals may be optimized as needed. The respiration information can be uploaded from the device and evaluated by a clinician.

Figure 6:
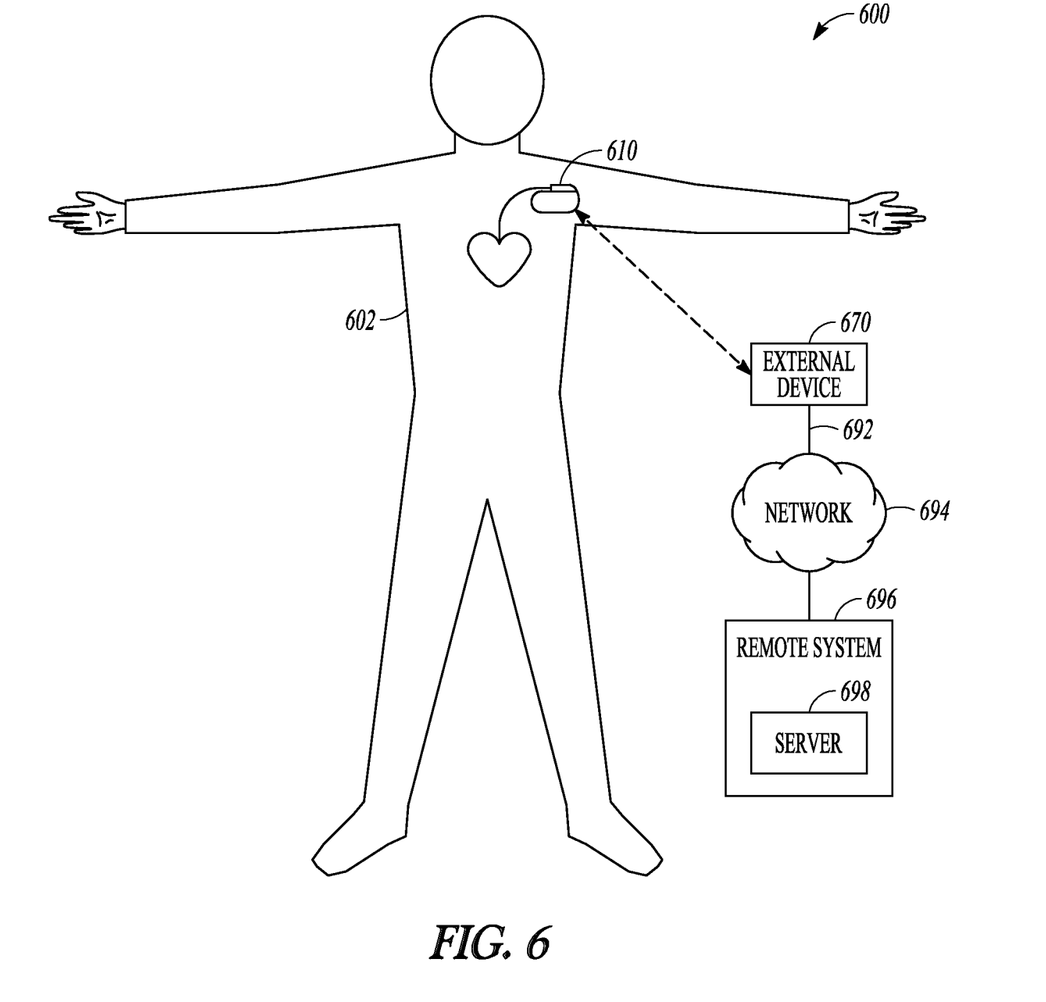
FIG. 6 is an illustration of portions of another example of a medical device system.

FIG. 6 is an illustration of portions of another system 600 that uses an IMD 610 to provide a therapy to a patient 602. The system 600 typically includes an external device 670 that communicates with a remote system 696 via a network 694. The network 694 can be a communication network such as a cellular telephone network or a computer network (e.g., the internet). In some examples, the external device includes a repeater and communicated via the network using a link 692 that may be wired or wireless. In some examples, the remote system 696 provides patient management functions and may include one or more servers 698 to perform the functions.

Optimizing the recording of the information can lead to more accurate information being collected by a device, which can lead to improved treatment of the patient's condition (e.g., for heart failure) and more effective device-based therapy provided to the patient.

ADDITIONAL DESCRIPTION AND EXAMPLES

Example 1 includes subject matter (such as an apparatus) comprising a respiration sensing circuit configured for coupling electrically to a plurality of electrodes and for sensing a respiration signal representative of respiration of a subject; a signal processing circuit electrically coupled to the respiration sensing circuit and configured to extract a respiration parameter from a sensed respiration signal and determine a signal performance metric for the sensed respiration signal using the respiration parameter; and a control circuit. The control circuit is configured to: initiate sensing of a plurality of respiration signals using different electrode combinations of the plurality of electrodes and determining of the signal performance metric for the sensed respiration signals; and enable an electrode combination from the plurality of electrodes and for use in monitoring respiration of the subject according to the signal performance metric.

In Example 2, the subject matter of Example 1 optionally includes a signal processing circuit configured to extract a measure of tidal volume from the sensed respiration signal, wherein the signal performance metric includes a signal-to-noise ratio (SNR) calculated using measured tidal volume.

In Example 3, the subject matter of one or both of Examples 1 and 2 optionally includes a signal processing circuit configured to extract a measure of respiration rate (RR) from the sensed respiration signal and monitor when RR information is unavailable in sensed respiration signals, wherein the signal performance metric for an electrode combination includes an amount of RR information available from respiration signals sensed using the electrode combination.

In Example 4, the subject matter of one or any combination of Example 1-3 optionally includes the plurality of electrodes and a device housing, wherein the plurality of electrodes include multiple electrodes configured to be implantable in one or more heart chambers of the subject and at least one electrode formed using the device housing, and wherein the electrode combinations include at least one electrode implantable in a heart chamber and the at least one electrode formed using the device housing.

In Example 5, the subject matter of one or any combination of Examples 1-3 optionally includes the plurality of electrodes and a device housing, wherein the plurality of electrodes include multiple electrodes included in a lead configured to be implantable in a left ventricle (LV) of the subject and at least one electrode formed using the device housing, wherein the electrode combinations include at least one electrode included in the lead and the at least one electrode formed using the device housing.

In Example 6, the subject matter of Example 5 optionally includes a lead configured to be implantable in a coronary vein of the left ventricle, wherein the signal processing circuit includes an impedance sensing circuit configured to determine impedance between the at least one electrode included in the lead and the at least one electrode formed using the device housing, and wherein the control circuit is configured to enable the electrode combination for use in monitoring respiration of the subject according to the signal performance metric and the determined impedance.

In Example 7, the subject matter of one or any combination of Examples 1-6 optionally includes a posture sensor circuit configured to provide a posture signal that includes posture information of the subject; and a posture calculation circuit configured to determine posture of the subject using the posture information, wherein the control circuit is configured to: initiate the sensing of the plurality of respiration signals using different electrode combinations of the plurality of electrodes and the determining of the signal performance metric for the sensed respiration signals according to a determined posture; and select the electrode combination for use in monitoring respiration of the subject according to the signal performance metric and the determined posture.

In Example 8, the subject matter of one or any combination of Examples 1-7 optionally includes a timer circuit integral to, or electrically coupled to the control circuit, wherein the control circuit is configured to: initiate the sensing of the plurality of respiration signals using different electrode combinations of the plurality of electrodes and the determining of the signal performance metric for the sensed respiration signals according to a time of day; and select the electrode combination for use in monitoring minute ventilation of the subject according to the signal performance metric and the time of day.

In Example 9, the subject matter of one or any combination of Examples 1-8 optionally includes a cardiac signal sensing circuit configured for coupling electrically to the plurality of electrodes and to sense cardiac activation within a subject's body using the electrodes; and a stimulus circuit configured for coupling electrically to the plurality of electrodes, wherein the control circuit is configured to select the electrode combination according to the signal performance metric for use in determining minute ventilation information of the subject and to adjust a cardiac pacing therapy parameter using the minute ventilation information.

Example 10 can include subject matter (such as an apparatus), or can optionally be combined with the subject matter of one or any combination of Examples 1-9 to include such subject matter, comprising an impedance sensing circuit configured for coupling electrically to a plurality of electrodes and for sensing an impedance signal representative of respiration of a subject; and a control circuit electrically coupled to the impedance sensing circuit. The control circuit is configured to: initiate sensing values of impedance of different electrode combinations of the plurality of electrodes; and determine an electrode combination from the plurality of electrodes according to the values of impedance for use with the impedance sensing circuit in monitoring respiration of the subject.

In Example 11, the subject matter of Example 10 optionally includes the plurality of electrodes and a housing, wherein the plurality of electrodes include multiple electrodes configured to be implantable in one or more heart chambers of the subject and at least one electrode formed using the housing, and wherein the electrode combinations include at least one electrode implantable in a heart chamber and the at least one electrode formed using the housing.

In Example 12, the subject matter of Example 10 optionally includes the plurality of electrodes and a housing, wherein the plurality of electrodes include multiple electrodes included in a lead configured to be implantable in a left ventricle (LV) of the subject and at least one electrode formed using the housing, wherein the electrode combinations include at least one electrode implantable in the LV and the at least one electrode formed using the housing.

In Example 13, the subject matter of Example 12 optionally includes a lead configured to be implantable in a coronary vein of the left ventricle, and wherein the selected electrode combination corresponds to the electrode combination determined to have lowest measured impedance between the at least one electrode included in the lead and the at least one electrode formed using the housing.

In Example 14, the subject matter of one or any combination of Examples 10-13 optionally includes a control circuit configured to select the electrode combination having the lowest impedance value for use in determining minute ventilation information for the subject.

In Example 15, the subject matter of Example 14 optionally includes a cardiac signal sensing circuit configured for coupling electrically to the plurality of electrodes and to sense cardiac activation within a subject's body using the electrodes; and a stimulus circuit configured for coupling electrically to the plurality of electrodes and to provide cardiac pacing therapy to the subject, wherein the control circuit is configured to adjust a cardiac pacing therapy parameter using the minute ventilation information.

In Example 16, the subject matter of one or any combination of Example 10-15 optionally includes a posture sensor circuit configured to provide a posture signal that includes posture information of the subject; and a posture calculation circuit configured to determine posture of the subject using the posture information, wherein the control circuit is configured to: initiate the sensing of the plurality of respiration signals using different electrode combinations of the plurality of electrodes and the determining of the signal performance metric for the sensed respiration signals according to a determined posture; and select the electrode combination having the lowest impedance value and according to the determined posture.

In Example 17, the subject matter of one or any combination of Example 10-16 optionally includes a timer circuit integral to, or electrically coupled to the control circuit, wherein the control circuit is configured to: initiate the sensing of the plurality of respiration signals using different electrode combinations of the plurality of electrodes and the determining of the signal performance metric for the sensed respiration signals according to a time of day; and select the electrode combination for use in monitoring minute ventilation of the subject according to the signal performance metric and the time of day.

Example 18 can include subject matter (such as an apparatus), or can optionally be combined with the subject matter of one or any combination of Examples 1-17 to include such subject matter, comprising a respiration sensing circuit configured for coupling electrically to a plurality of electrodes and for sensing a respiration signal representative of respiration of a subject; a cardiac signal sensing circuit configured for coupling electrically to the plurality of electrodes and to sense cardiac activation of the subject using the electrodes; a stimulus circuit configured for coupling electrically to the plurality of electrodes and to provide pacing pulse stimulation energy to the subject; and a control circuit. The control circuit is configured to initiate delivery of pacing pulses using combinations of the electrodes that include one electrode of the plurality of electrodes as a pacing cathode and the other electrodes as the pacing anode; initiate sensing of cardiac activation resulting from the pacing pulses; determine a cardiac capture pulse energy level threshold for the electrodes using the sensed cardiac activation; and enable an electrode combination from the plurality of electrodes having the highest determined cardiac capture pulse energy level threshold for use in monitoring respiration of the subject.

In Example 19, the subject matter of Example 18 optionally includes the plurality of electrodes and a housing, wherein the plurality of electrodes include multiple electrodes included in a lead configured to be implantable in a left ventricle (LV) of the subject and at least one electrode formed using the housing, wherein the electrode combinations include at least one electrode implantable in the LV and the at least one electrode formed using the housing.

In Example 20, the subject matter of Example 19 optionally includes a control circuit configured to select the electrode combination for use in determining minute ventilation information of the subject and to adjust a cardiac pacing therapy parameter using the minute ventilation information.

Example 21 can include subject matter (such as a method of controlling operation of an ambulatory medical device, a means for performing acts, or a machine-readable medium including instructions that, when performed by the machine, cause the machine to perform acts), or can optionally be combined with the subject matter of one or any combination of Examples 1-20 to include such subject matter, comprising: sensing a plurality of respiration signals representative of respiration of a subject using different electrode combinations of a plurality of electrodes; extracting a respiration parameter from the sensed respiration signals; determining a signal performance metric for the sensed respiration signals using the respiration parameters; and enabling an electrode combination from the plurality of electrodes for use in monitoring respiration of the subject according to the signal performance metric.

In Example 22, the subject matter of Example 21 can optionally include extracting a measure of tidal volume from the sensed respiration signals, wherein determining the signal performance metric includes determining a signal-to-noise ratio (SNR) calculated using measured tidal volume.

In Example 23, the subject matter of one or both of Examples 21 and 22 optionally includes extracting a measure of respiration rate (RR) from the sensed respiration signal and monitoring when RR information is unavailable in the sensed respiration signals, wherein determining the signal performance metric includes determining an amount of RR information available from respiration signals sensed using the electrode combination.

In Example 24, the subject matter of one or any combination of Examples 21-23 optionally includes sensing the plurality of respiration signals using multiple electrodes combinations that include at least one electrode implantable in a heart chamber and the at least one electrode formed using a housing of the ambulatory medical device.

In Example 25, the subject matter of one or any combination of Examples 21-24 can optionally include sensing the plurality of respiration signals using multiple electrodes combinations that include at least one electrode included in a lead configured to be implantable in a left ventricle (LV) of the subject and at least one electrode formed using a housing of the ambulatory medical device.

In Example 26, the subject matter of one or any combination of Examples 21-25 optionally includes adjusting an electrical stimulus provided by the ambulatory medical using the minute ventilation information.

Example 27 can include, or can optionally be combined with any portion or combination of any portions of any one or more of Examples 1-26 to include, subject matter that can include means for performing any one or more of the functions of Examples 1-26, or a machine-readable medium including instructions that, when performed by a machine, cause the machine to perform any one or more of the functions of Examples 1-26.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a respiration sensing circuit configured for coupling electrically to a plurality of electrodes and for sensing a respiration signal representative of respiration of a subject;
   a signal processing circuit electrically coupled to the respiration sensing circuit and configured to extract a respiration parameter from a sensed respiration signal and determine a signal performance metric for the sensed respiration signal using the respiration parameter; and
   a control circuit configured to:
      determine one or more electrodes of the plurality of electrodes that are non-contacting electrodes, wherein the one or more non-contacting electrodes are less likely to be in contact with coronary vein tissue of the subject than the other electrodes;
      initiate sensing of a plurality of respiration signals using different electrode combinations of the plurality of electrodes, each of the electrode combinations including at least one of the one or more non-contacting electrode; and
      determining the signal performance metric for the plurality of sensed respiration signals; and
      select one of the electrode combinations for use in monitoring respiration of the subject according to the signal performance metric.

2. The apparatus of claim 1, wherein the signal processing circuit is configured to extract a measure of tidal volume from the sensed respiration signal, wherein the signal performance metric includes a signal-to-noise ratio (SNR) calculated using measured tidal volume.

3. The apparatus of claim 1, wherein the signal processing circuit is configured to extract a measure of respiration rate (RR) from the sensed respiration signal and monitor when RR information is unavailable in sensed respiration signals, wherein the signal performance metric for an electrode combination includes an amount of RR information available from respiration signals sensed using the electrode combination.

4. The apparatus of claim 1, including the plurality of electrodes and a device housing, wherein the plurality of electrodes include multiple electrodes configured to be implantable in or adjacent to one or more heart chambers of the subject and at least one electrode formed using the device housing, and wherein the electrode combinations include at least one electrode implantable in or adjacent to a heart chamber.

5. The apparatus of claim 1, including the plurality of electrodes and a device housing, wherein the plurality of electrodes include multiple electrodes included in a lead configured to be implantable in or adjacent to a left ventricle (LV) of the subject and at least one electrode formed using the device housing, wherein the electrode combinations include at least one electrode included in the lead and the at least one electrode formed using the device housing.

6. The apparatus of claim 5, wherein the lead is configured to be implantable in a coronary vein of the left ventricle, wherein the signal processing circuit includes an impedance sensing circuit configured to determine impedance between the at least one electrode included in the lead and the at least one electrode formed using the device housing, and wherein the control circuit is configured to enable the electrode combination for use in monitoring respiration of the subject according to the signal performance metric and having a lowest determined impedance.

7. The apparatus of claim 1, including a posture sensor circuit configured to provide a posture signal that includes posture information of the subject; and a posture calculation circuit configured to determine posture of the subject using the posture information, wherein the control circuit is configured to: initiate the sensing of the plurality of respiration signals using different electrode combinations of the plurality of electrodes and the determining of the signal performance metric for the sensed respiration signals according to a determined posture; and select the electrode combination for use in monitoring respiration of the subject according to the signal performance metric and the determined posture.

8. The apparatus of claim 1, including a timer circuit integral to, or electrically coupled to the control circuit, wherein the control circuit is configured to: initiate the sensing of the plurality of respiration signals using different electrode combinations of the plurality of electrodes and the determining of the signal performance metric for the sensed respiration signals according to a time of day; and select the electrode combination for use in monitoring minute ventilation of the subject according to the signal performance metric and the time of day.

9. The apparatus of claim 1, including: a cardiac signal sensing circuit configured for coupling electrically to the plurality of electrodes and to sense cardiac activation within a subject's body using the electrodes; and a stimulus circuit configured for coupling electrically to the plurality of electrodes, wherein the control circuit is configured to select the electrode combination according to the signal performance metric for use in determining minute ventilation information of the subject and to adjust a cardiac pacing therapy parameter using the minute ventilation information.

10. A method of controlling operation of an ambulatory medical device connectable to a plurality of electrodes, the method comprising:
determining one or more electrodes of the plurality of electrodes that are non-contacting electrodes, wherein the one or more non-contacting electrodes are less likely to be in contact with coronary vein tissue of the subject than the other electrodes;
sensing of a plurality of respiration signals using different electrode combinations of the plurality of electrodes, each of the electrode combinations including at least one of the one or more non-contacting electrode, wherein the respiration signal is representative of respiration of a subject;
extracting a respiration parameter from the sensed respiration signals and determining a signal performance metric for the sensed respiration signals; and
selecting one of the electrode combinations for use in monitoring respiration of the subject according to the signal performance metric.

11. The method of claim 10, including extracting a measure of tidal volume from the sensed respiration signal, wherein the signal performance metric includes a signal-to-noise ratio (SNR) calculated using measured tidal volume.

12. The method of claim 10, including extracting a measure of respiration rate (RR) from the sensed respiration signal and monitor when RR information is unavailable in sensed respiration signals, wherein the signal performance metric for an electrode combination includes an amount of RR information available from respiration signals sensed using the electrode combination.

13. The method of claim 10, wherein the different electrode combinations include at least one electrode implantable in or adjacent to a heart chamber and the at least one electrode formed using the device housing.

14. The method of claim 10, wherein the plurality of electrodes include multiple electrodes included in a lead configured to be implantable in or adjacent to a left ventricle (LV) of the subject and at least one electrode formed using the device housing, wherein the electrode combinations include at least one electrode included in the lead and the at least one electrode formed using the device housing.

15. The method of claim 14, including determining impedance between electrode combinations including at least one electrode included in a lead configured to be implantable in a coronary vein of the left ventricle and the at least one electrode formed using the device housing, and enable electrode combination for use in monitoring respiration of the subject according to the signal performance metric and having a lowest determined impedance.

16. The method of claim 10, including:
sensing the plurality of respiration signals using different electrode combinations of the plurality of electrodes;
determining the signal performance metric for the sensed respiration signals according to a device-determined patient posture; and
selecting the electrode combination for use in monitoring respiration of the subject according to the signal performance metric and the determined posture.

17. The method of claim 10, including:
sensing the plurality of respiration signals using different electrode combinations of the plurality of electrodes;
determining the signal performance metric for the sensed respiration signals according to a time of day; and
selecting the electrode combination for use in monitoring minute ventilation of the subject according to the signal performance metric and the time of day.

18. The method of claim 10, including:
sensing cardiac activation within a subject's body using the plurality of electrodes;
selecting the electrode combination according to the signal performance metric for use in determining minute ventilation information of the subject; and
adjusting a cardiac pacing therapy parameter using the minute ventilation information.

19. The method of claim 10, including:
delivering pacing pulses using combinations of the plurality of electrodes that include one electrode of the plurality of electrodes as a pacing cathode and the other electrodes as the pacing anode;
sensing cardiac activation resulting from the pacing pulses;
determining a cardiac capture pulse energy level threshold for the electrodes using the sensed cardiac activation; and
enabling an electrode combination from the plurality of electrodes having the highest determined cardiac capture pulse energy level threshold for use in monitoring respiration of the subject.

20. The method of claim 19, including:
selecting the electrode combination for use in determining minute ventilation information of the subject; and
adjusting a cardiac pacing therapy parameter using the minute ventilation information.

* * * * *